(12) United States Patent
Burke et al.

(10) Patent No.: US 7,108,686 B2
(45) Date of Patent: Sep. 19, 2006

(54) IMPLANTABLE, REFILLABLE INFUSION DEVICE AND SEPTUM REPLACEMENT KIT

(75) Inventors: Paul Burke, Bellingham, MA (US); Kenneth A. Fine, Sharon, MA (US)

(73) Assignee: Bard Access Systems, Inc., Salt Lake City, UT (US)

( * ) Notice: Subject to any disclaimer, the term of this patent is extended or adjusted under 35 U.S.C. 154(b) by 391 days.

(21) Appl. No.: 10/169,821

(22) PCT Filed: Jan. 11, 2001

(86) PCT No.: PCT/US01/00846

§ 371 (c)(1), (2), (4) Date: Nov. 13, 2002

(87) PCT Pub. No.: WO01/51108

PCT Pub. Date: Jul. 19, 2001

(65) Prior Publication Data

US 2003/0208184 A1   Nov. 6, 2003

Related U.S. Application Data

(63) Continuation of application No. 09/481,298, filed on Jan. 11, 2000, now Pat. No. 6,764,472.

(51) Int. Cl.
*A61K 9/22* (2006.01)
*A61M 37/00* (2006.01)
*A61M 31/00* (2006.01)

(52) U.S. Cl. .................. 604/891.1; 604/131; 604/140; 604/145; 604/288.02

(58) Field of Classification Search ............ 604/890.1, 604/891.1, 19, 21, 93.01, 131–134, 140–141, 604/143, 145–146, 151, 153, 246–250, 256, 604/288.01–288.04
See application file for complete search history.

(56) References Cited

U.S. PATENT DOCUMENTS

| 3,682,315 A | 8/1972 | Haller |
|---|---|---|
| 3,731,681 A | 5/1973 | Blackshear et al. |
| 3,840,009 A * | 10/1974 | Michaels et al. ........ 604/892.1 |
| 3,896,806 A | 7/1975 | Wichterle |

(Continued)

FOREIGN PATENT DOCUMENTS

DE     28 05 354     9/1978

(Continued)

*Primary Examiner*—Nicholas D. Lucchesi
*Assistant Examiner*—Catherine S. Williams
(74) *Attorney, Agent, or Firm*—Nields & Lemack (57) ABSTRACT

An implantable infusion device (10) includes a lightweight, inert housing (12) which contains an infusate (18) for administration to a patient, and an enclosed, gas-impermeable variable volume chamber (30) which contains a pressure source, such as propellant, mechanical spring, or the like. The variable volume chamber may be in the form of a rigid-walled expandable bellows structure or a nonstretchable flexible bag and is attached to the housing so as not to obstruct the entry port for introduction of infusate. A recharging fluid flow path (31) is provided adjacent to where the variable volume chamber is attached to the housing. The infusate is delivered from the device via a catheter in response to expansion of the variable volume chamber against the volume of infusate in the housing. A separate bolus injection port (38) is provided which allows infusate to be safely introduced directly into the catheter and overrides the controlled pressure-driven delivery. The lightweight housing may include integrally formed needle stops (32 and 34) and suture fastening loops (36).

49 Claims, 5 Drawing Sheets

U.S. PATENT DOCUMENTS

| | | | |
|---|---|---|---|
| 3,951,147 A | 4/1976 | Tucker et al. | |
| 3,971,376 A | 7/1976 | Wichterle | |
| 4,146,029 A | 3/1979 | Ellinwood, Jr. | |
| 4,193,397 A | 3/1980 | Tucker et al. | |
| 4,221,219 A | 9/1980 | Tucker | |
| 4,258,711 A | 3/1981 | Tucker et al. | |
| 4,286,584 A | 9/1981 | Sampson et al. | |
| 4,299,220 A | 11/1981 | Dorman | |
| 4,360,019 A | 11/1982 | Portner et al. | |
| 4,368,737 A | 1/1983 | Ash | |
| 4,373,527 A | 2/1983 | Fischell | |
| 4,417,888 A | 11/1983 | Cosentino et al. | |
| 4,447,237 A | 5/1984 | Frisch et al. | |
| 4,464,178 A | 8/1984 | Dalton | |
| 4,490,137 A | 12/1984 | Moukheibir | |
| 4,496,343 A | 1/1985 | Prosl et al. | |
| 4,505,710 A | 3/1985 | Collins | |
| 4,525,165 A | 6/1985 | Fischell | |
| 4,543,088 A | 9/1985 | Bootman et al. | |
| 4,552,561 A | 11/1985 | Eckenhoff et al. | |
| 4,573,994 A | 3/1986 | Fischell et al. | |
| 4,576,211 A | 3/1986 | Valentini et al. | |
| 4,588,394 A | 5/1986 | Schulte et al. | |
| 4,604,090 A | 8/1986 | Reinicke | |
| 4,619,652 A | 10/1986 | Eckenhoff et al. | |
| 4,655,765 A | 4/1987 | Swift | |
| 4,673,391 A | 6/1987 | Kondo et al. | |
| 4,687,468 A | 8/1987 | Gianturco | |
| 4,692,146 A | 9/1987 | Hilger | |
| 4,692,147 A | 9/1987 | Duggan | |
| 4,695,273 A | 9/1987 | Brown | |
| 4,710,174 A | 12/1987 | Moden et al. | |
| 4,714,462 A | 12/1987 | DiDomenico | |
| 4,718,893 A | 1/1988 | Dorman et al. | |
| 4,731,051 A | 3/1988 | Fischell | |
| 4,760,837 A | 8/1988 | Petit | |
| 4,781,680 A | 11/1988 | Redmond et al. | |
| 4,784,645 A | 11/1988 | Fischell | |
| 4,784,646 A | 11/1988 | Feingold | |
| 4,810,246 A | 3/1989 | Frisch et al. | |
| 4,820,273 A | 4/1989 | Reinicke | |
| 4,826,487 A | 5/1989 | Winter | |
| 4,832,054 A | 5/1989 | Bark | |
| 4,834,713 A | 5/1989 | Suthanthiran | |
| 4,857,053 A | 8/1989 | Dalton | |
| 4,871,351 A | 10/1989 | Feingold | |
| 4,886,501 A | 12/1989 | Johnston et al. | |
| 4,892,518 A | 1/1990 | Cupp et al. | |
| 4,904,241 A | 2/1990 | Bark | |
| 4,922,926 A | 5/1990 | Hirschberg et al. | |
| 4,931,050 A | 6/1990 | Idriss | |
| 4,955,861 A | 9/1990 | Enegren et al. | |
| 4,969,873 A | 11/1990 | Steinbach et al. | |
| 4,978,338 A | 12/1990 | Melsky et al. | |
| 5,006,115 A | 4/1991 | McDonald | |
| 5,009,644 A | 4/1991 | McDonald | |
| 5,045,064 A | 9/1991 | Idriss | |
| 5,053,031 A | 10/1991 | Borsanyi | |
| 5,061,242 A | 10/1991 | Sampson | |
| 5,085,656 A | 2/1992 | Polaschegg | |
| 5,088,983 A | 2/1992 | Burke | |
| 5,135,497 A | 8/1992 | Hessel et al. | |
| 5,135,502 A | 8/1992 | Koenig, Jr. et al. | |
| 5,137,529 A | 8/1992 | Watson et al. | |
| 5,167,625 A | 12/1992 | Jacobsen et al. | |
| 5,167,633 A | 12/1992 | Mann et al. | |
| 5,167,638 A | 12/1992 | Felix et al. | |
| 5,176,644 A * | 1/1993 | Srisathapat et al. | 604/141 |
| 5,176,653 A | 1/1993 | Metals | |
| 5,180,365 A | 1/1993 | Ensminger et al. | |
| 5,201,728 A | 4/1993 | Giampapa | |
| 5,207,644 A | 5/1993 | Strecker | |
| 5,248,301 A | 9/1993 | Koenig, Jr. et al. | |
| 5,281,210 A | 1/1994 | Burke et al. | |
| 5,318,540 A | 6/1994 | Athayde et al. | |
| 5,328,465 A | 7/1994 | Kratoska et al. | |
| 5,368,571 A | 11/1994 | Horres, Jr. | |
| 5,395,324 A | 3/1995 | Hinrichs et al. | |
| 5,443,450 A | 8/1995 | Kratoska et al. | |
| 5,445,616 A | 8/1995 | Kratoska et al. | |
| 5,507,737 A | 4/1996 | Palmskog | |
| 5,514,103 A | 5/1996 | Srisathapat et al. | |
| 5,527,277 A | 6/1996 | Ensminger et al. | |
| 5,527,307 A | 6/1996 | Srisathapat et al. | |
| 5,551,849 A | 9/1996 | Christiansen | |
| 5,556,381 A | 9/1996 | Ensminger et al. | |
| 5,558,640 A | 9/1996 | Pfeiler et al. | |
| 5,575,770 A * | 11/1996 | Melsky et al. | 604/288.04 |
| 5,607,418 A | 3/1997 | Arzbaecher | |
| 5,637,088 A | 6/1997 | Wenner et al. | |
| 5,667,504 A | 9/1997 | Baumann et al. | |
| 5,695,490 A | 12/1997 | Flaherty et al. | |
| 5,707,361 A | 1/1998 | Slettenmark | |
| 5,722,957 A | 3/1998 | Steinbach | |
| 5,752,930 A | 5/1998 | Rise et al. | |
| 5,769,823 A | 6/1998 | Otto | |
| 5,785,681 A | 7/1998 | Indravudh | |
| 5,814,019 A * | 9/1998 | Steinbach et al. | 604/131 |
| 5,836,915 A | 11/1998 | Steinbach et al. | |
| 5,897,528 A | 4/1999 | Schultz | |
| 5,908,414 A | 6/1999 | Otto et al. | |
| 5,925,017 A | 7/1999 | Kriesel et al. | |
| 5,925,030 A | 7/1999 | Gross et al. | |
| 5,928,195 A | 7/1999 | Malamud et al. | |
| 5,957,890 A | 9/1999 | Mann et al. | |
| 5,976,109 A | 11/1999 | Heruth | |
| 6,039,712 A | 3/2000 | Fogarty et al. | |
| 6,048,328 A | 4/2000 | Haller et al. | |
| 6,053,891 A | 4/2000 | DeCampli | |
| 6,152,898 A | 11/2000 | Olsen | |
| 6,168,575 B1 | 1/2001 | Soltanpour | |
| 6,228,050 B1 | 5/2001 | Olsen et al. | |
| 6,238,367 B1 | 5/2001 | Christiansen et al. | |
| 6,280,416 B1 | 8/2001 | Van Antwerp et al. | |
| 6,283,943 B1 | 9/2001 | Dy et al. | |
| 6,283,949 B1 | 9/2001 | Roorda | |
| 6,572,583 B1 | 6/2003 | Olsen et al. | |
| 6,589,198 B1 | 7/2003 | Soltanpour et al. | |
| 6,645,176 B1 | 11/2003 | Christenson et al. | |
| 6,764,472 B1 * | 7/2004 | Burke et al. | 604/288.04 |
| 2003/0082507 A1 | 5/2003 | Stypulkowski | |
| 2003/0088236 A1 | 5/2003 | Johnson et al. | |

FOREIGN PATENT DOCUMENTS

| | | |
|---|---|---|
| DE | 290 585 | 10/1983 |
| DE | 689 03 565 | 6/1993 |
| EP | 0 335 671 | 10/1989 |
| EP | 0 858 814 | 1/1998 |
| WO | 80/02377 | 11/1980 |

* cited by examiner

IMPLANTABLE, REFILLABLE INFUSION DEVICE AND SEPTUM REPLACEMENT KIT

This application is a national stage of PCT/US01/00846 which is a continuation of U.S. patent application Ser. No. 09/481,298 filed Jan. 11, 2000 now U.S. Pat. No. 6,764,472.

TECHNICAL FIELD

The invention relates to implantable infusion devices for controllable in vivo delivery of drugs to a patient.

BACKGROUND OF THE INVENTION

Implantable infusion devices provide a patient with an vivo source of a drug to be administered, in a device which permits controlled delivery of the drug over a predetermined time period. Certain drugs, such as, for example, chemotherapy drugs and opioids, may be most effective if administered at a constant dose rate, instead of at discrete intervals.

A typical infusion device or pump includes a hermetically sealed outer housing which holds a vapor pressure fluid or other means for exerting a compressive force on a compressible or flexible inner drug reservoir which communicates with a drug delivery port. Alternatively, the drug may be disposed in the outer housing, with a propellant disposed in the inner housing. When the outer housing is filled with the drug, the propellant in the inner housing is compressed and changes state from a vapor to a liquid, thereby recharging the driving mechanism of the device. In still other embodiments, the outer housing may be divided into two chambers separated by a liquid-impermeable diaphragm. One chamber contains the drug and includes a drug delivery port, and the other chamber contains a propellant or spring member for exerting a force against the diaphragm so as to expel the drug through the delivery port.

The infusion device must meet numerous requirements for safety and efficacy. For example, the housing material must not react with body fluids or with the drugs and propellants inside the housing. Further, the membrane or flexible barrier between the chambers must not leak and must be impermeable to gas-phase fluids so as to prevent contamination of the drug with the propellant. Since the device is designed for implantation into a patient, great care must be taken to prevent any leakage of either the drug or the propellant into the patient's body. In addition, the device is desirably as small and lightweight as possible so as to cause minimum invasive trauma, discomfort and disfigurement to the patient, yet sufficiently large to provide a useful therapeutic dosage of the drug being administered and minimize the frequency with which the device must be recharged. It is desirable to make the pump refillable so that it need not be surgically removed and replaced when the drug is depleted. However, refillability of the pump requires a port which is either outside of the skin or transcutaneously accessible without introducing infection or risking the release of an excessive and potentially harmful amount of the drug into the patient. Also, in those devices in which a propellant is contained within a flexible bag which expands and contracts in response to changes in the propellant pressure, it is necessary to ensure that introduction of the drug to the drug reservoir surrounding the propellant bag is not impeded by the presence and location of the bag in the reservoir and/or does not puncture or pinch the bag. Thus, it may be necessary to affix the repellant chamber or bag to the housing so as to avoid such problems. There is the additional problem of ensuring that the drug reservoir can be fully depleted and refilled, for optimum efficiency of the device.

Administration of a desired dosage of a drug over a period of time may require a controllable, constant flow of the drug from the device. However, as the drug is depleted from the reservoir, or if the force exerted on the drug reservoir cannot be controlled, a constant dose rate may be difficult to sustain.

U.S. Pat. No. 3,840,009 to Michaels et al. discloses a vapor pressure drug delivery device which has two chambers separated by a flexible wall or bladder. The outer chamber contains a drug to be administered to a patient, and the inner chamber contains a pressure fluid which expands to conform to the shape of the outer chamber, thereby enabling expulsion of substantially all of the drug within the outer chamber. The pressure fluid is maintained at a positive pressure at the temperature at which the device is used, so that no external power source is required.

U.S. Pat. No. 5,167,633 to Mann et al. discloses a medication infusion pump in which a constant pressure is exerted on a liquid medication to be administered. The pump includes a pressure reservoir in the form of a hollow enclosure with at least one flexible wall for containing a pressure fluid. The medication to be administered is outside of the pressure reservoir. The pressure fluid undergoes a phase change from a liquid to a vapor so as to expel the drug from the pump. The Mann et al. device is maintained at a negative pressure at the temperature of use to avoid leakage of medication from the pump into the patient.

U.S. Pat. No. 5,514,103 to Srisathapat et al. discloses a medication infusion pump including a drug reservoir and a pressure fluid reservoir which are separated by a movable wall or flexible bag. The pressure fluid reservoir includes a spacer therein to prevent contraction of the pressure fluid reservoir below a minimum volume which is slightly greater than the liquid phase volume of the pressure fluid, so that a portion of the pressure fluid always remains in a vapor phase. As a result, even when the drug reservoir is completely filled, the pressure fluid is not entirely in the liquid phase. Thus, additional energy to reinstate a vapor phase is not required.

U.S. Pat. No. 3,951,147 to Tucker et al. discloses a refillable implantable infusate pump in which a bellows containing a drag is contained within a housing which is filled with a pressure fluid or propellant. The Tucker et al. pump includes a filtering chamber to ensure removal of debris from the infusate drug prior to its delivery to the patient.

U.S. Pat. No. 5,045,064 to Idriss discloses a constant pressure implantable pump which employs shape-memory metal bands around a reservoir containing a fluid to be infused. The bands compress the reservoir containing the fluid to be infused, thereby eliminating the need for a propellant.

U.S. Pat. No. 5,395,324 to Hinrichs et al. discloses an infusion pump having a primary entry port leading to a drug reservoir, a separate bolus port leading to a bolus chamber, and means for ensuring that the bolus chamber is not inadvertently filled with the drug intended for the primary drug reservoir.

U.S. Pat. No. 5,769,823 to Otto discloses implantable infusion pump which comprises a plastic housing, a bellows chamber enclosing a propellant, and two separate resilient plastic bags enclosing an infusate. The bags are surrounded by glycerin or the like which binds with any propellant passing through the bellows wall into the housing, thereby preventing passage of the propellant through the housing into the patient.

U.S. Pat. No. 5,575,770 to Melsky et al. discloses an implantable infusion pump having 4 valve-actuated bolus delivery chamber. Inadvertent administration of an overdose to the patient through the bolus delivery chamber is prevented by a design which requires the use of a side-access delivery needle, which is inserted through a pair of septa which are spaced apart to define a bolus chamber. The tip of the needle extends beyond the lower septum and depresses a lever to actuate the normally-closed valve. The side opening of the needle is disposed between the septa in lo the bolus chamber for delivery of the bolus dose to the bolus chamber. The design prevents erroneous dose delivery by requiring the simultaneous opening of the valve with delivery of the drug into the bolus using a side-access delivery needle.

It would be advantageous to provide an implantable infusion pump which is of simple construction and operation, made of lightweight materials, inexpensive to manufacture, efficient in the delivery of medicine, and easy to refill.

SUMMARY OF THE INVENTION

An implantable infusion device is disclosed having a housing including an inner wall and having an interior region defined at least in part by the inner wall. At least a portion of the interior region defines an infusate reservoir adapted to store an infusate therein for delivery to a patient. A closed variable volume chamber is disposed within the interior region of the housing and is coupled to an internal portion of the housing. The variable volume chamber contains a pressure source.

In one embodiment, an infusate recharging fluid flow path is provided and adapted to carry infusate from a first point external to the housing to a region adjacent the internal portion of the housing to recharge the infusate reservoir.

In a second embodiment, an infusate recharging fluid flow path is provided and adapted to carry infusate from a first point external to the housing to the infusate reservoir. An exit fluid flow path is provided and adapted to carry infusate from the infusate reservoir to a second point external to the housing. A bolus port is provided on the device in fluid communication with the exit fluid flow path.

In a third embodiment, the variable volume chamber is free floating within the interior region of the housing and a fluid flow path is provided to carry infusate between a point external to the housing and the interior region of the housing. A spacer is supported on at least one of the housing and the variable volume chamber to maintain the fluid flow path unobstructed.

The housing of the device may be any shape, and is preferably made of a biologically inert material. The variable volume chamber supported within the housing may be free-floating, or may be attached to the inner wall of the housing. The variable volume chamber may be any such device known to those of ordinary skill in the art, such as an accordion-type bellows, a bag or an envelope. A fluid or infusate may be contained by the remaining space or principal reservoir in the interior region of the housing. The variable volume chamber contains a pressure source that will cause the chamber to expand and expel the fluid from the housing via an exit fluid flow path. Preferably, the recharging fluid flow path extends from a point external to the housing to the principal reservoir. The recharging fluid flow path has an entry port which may be sealed by a self-sealing septum, which is provided to refill the principal reservoir of the housing with infusate. The recharging fluid flow path is preferably located at a coupling region between the variable volume chamber and the housing. The path may be made of channels 45 (FIG. 3) to assist in dispersing the fluid to the principal reservoir. Preferably, the rechargeable fluid flow path includes a fluid dispersal flow path at the coupling region.

A separate bolus port may also be provided on the implantable infusion device. The bolus port has direct access to the exit fluid flow path, thereby bypassing the pressure source-driven principal reservoir. A self-sealing septum may also be provided in the bolus port. Preferably, the bolus port includes two spaced-apart self-sealing septa forming a bolus reservoir therebetween such that a special delivery needle with an opening displaced from a tip of the needle is used to deliver fluid to the bolus reservoir.

According to one aspect of the invention, there is provided an implantable infusion device, comprising a housing having an annular portion with an inner wall defining an interior region having a width dimension D and extending along a central axis, a bottom portion extending from the annular portion and spanning a first end of the interior region, and a too portion extending from the annular portion and spanning a second end of the interior region and being opposite the bottom portion, the interior region being substantially closed. The device further includes a closed fluid-impermeable hollow bellows extending from one of the top and bottom portions of the housing and defining a variable volume region therein and having a plurality of serially coupled annular members extending between top and bottom portions of the bellows. Junctions of the coupled annular members are coupled with flexures. The bellows has a maximum outer width dimension D' where D' is less than D. The portion of the housing from which the bellows extends includes a substantially planar annular peripheral portion disposed about a central portion. A pressure source is contained within the variable volume region of the bellows. The bellows is disposed within the interior region of the housing and rigidly coupled to the portion of the housing from which it extends. The annular members, of the bellows are spaced apart from the annular portion of the housing. The housing includes a recharging fluid flow path from points external to the housing to a region adjacent to the central portion of the portion of the housing from which the bellows extends. The housing further defines a fluid exit flow path extending from the region between the bellows and the annular portion of the housing to points external to the housing.

The device may include a pierceable, self-sealing septum disposed in the recharging fluid flow path and may further include a recharging fluid reservoir disposed along the recharging fluid flow path. The septum may be removable from the housing.

The device may include at least one of a flow restrictor and/or a filter disposed along the fluid exit flow path.

In one embodiment, the housing is made of a gas-impermeable material, and the bellows which encloses the pressure source is made of a substantially rigid, gas-impermeable material. In a preferred embodiment, the bellows is hermetically sealed.

The pressure source comprises one or more of the group consisting of multiple-phase fluids, strings, shape memory metal alloys, Belville washers, and compressible materials. In one embodiment, a multiple-phase fluid propellant is present in at least one of a liquid phase and a gas phase within the variable volume region of the bellows as a function of ambient temperature. Conversion of thy propellant fluid from a liquid phase to a gas phase increases the volume displaced by the bellows in the interior region of the housing, thereby exerting a force on a fluid external to the bellows in the housing so as to provide a substantially constant flow rate of thy fluid through the fluid exit flow path.

In one embodiment, the propellant is disposed in the variable volume region of the bellows at a pressure which is not less than atmospheric pressure at ambient temperature.

In one embodiment, the central portion of the bellows is offset from the plane of the annular peripheral portion of the bellows. A central region of the portion of the housing from which the bellows extends is correspondingly offset from the plane of the annular portion of the housing. The offset central region of the housing substantially nests within the offset central portion of the bellows.

In one embodiment, the housing and bellows are cylindrical.

The device can further include a separate bolus port in fluid communication with the fluid exit flow path. The bolus port can include a pair of septa which are spaced apart to define a bolus reservoir therebetween. A side-access delivery needle having an opening near the center of its length is required to delivery a bolus dose of the infusate to the bolus reservoir.

In one embodiment, the bellows extends from the top potion of the housing. In another embodiment, the bellows extends from the bottom portion of the housing.

According to another aspect of the invention, there is provided an implantable infusion device, comprising a housing having an annular portion with an inner wall defining an interior region having a width dimension D and extending along a central axis, a bottom portion extending from the annular portion and spanning a first end of the interior region, and a top portion extending from the annular portion and spanning a second end of the interior region, the top portion being opposite the bottom portion, the interior region being substantially closed. The device further includes a closed fluid-impermeable hollow bellows disposed about a variable volume region and having a top member, a bottom member, and a plurality of serially coupled annular members extending therebetween. Junctions of the coupled annular members are coupled with flexures. The bellows has a maximum outer width dimension D' where D' is less than D. At least one of the top and bottom members includes a substantially planar annular peripheral portion disposed about a central portion. A pressure source is contained within the variable volume region of the bellows, and the bellows is disposed within the interior region of the housing with one of the top and bottom members facing and rigidly coupled to a corresponding portion of the housing. The annular members of the bellows are spaced apart from the annular portion of the housing. The housing includes a recharging fluid flow path from points external to the housing to a region adjacent to the central portion of one of the top and bottom members of the bellows. The region of coupling between the housing and the bellows defines a fluid dispersal flow path from the region adjacent to the central portion of the coupled member of the bellows to a region between the annular members of the bellows and the annular portion of the housing. The housing further defines a fluid exit flow path extending from the region between the bellows and the annular portion of the housing to points external to the housing.

In one embodiment, a central portion of at least one of the top and bottom members of the bellows is offset from the plane of the annular peripheral portion of the top and bottom members of the bellows. A central region of the portion of the housing which is coupled to the bellows is correspondingly offset from the plane of the annular portion of the housing, so that the offset central region of the portion of the housing which is coupled to the bellows nests within the central portion of the coupled portion of the bellows.

In one embodiment, the bellows is coupled to the top portion of the housing. In another embodiment, this bellows is coupled to the bottom portion of the housing.

According to still another aspect of the invention, there is provided a septum replacement kit for an enclosed device which is sealed with a septum, wherein the enclosed device defines a fluid reservoir, a fluid flow inlet and a fluid flow outlet. The kit comprises a compressible septum adapted to sealingly engage in the fluid flow inlet of the reservoir, and a septum installation tool adapted to compress the septum to a nominal insertion size, maintain the nominal insertion size of the septum prior to installation of the septum, and install the septum in the fluid flow inlet of the reservoir.

The septum installation tool preferably comprises a tubular member adapted for insertion into the fluid flow inlet of the reservoir, an opening in the tubular member for insertion and retention of the septum therein, and a plunger member disposable in the tubular member for expulsion of the septum from the tubular member. Insertion of the septum into the tubular member compresses the septum. Expulsion of the septum from the tubular member into the fluid inlet reservoir permits the septum to expand to fill in and seal the fluid inlet reservoir.

The septum is preferably made of a pierceable, self-sealing elastomeric or rubber-like material.

These and other objects and advantages of the invention will in part be obvious and will in part appear hereinafter. The invention accordingly comprises the apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be made to the following detailed description taken in connection with the accompanying drawings, in which.

Like features in the drawings are indicated with like numerals.

DETAILED DESCRIPTION OF THE DRAWINGS

The infusion device of the present invention may be configured to have a relatively low profile, as shown in FIGS. 1, 3, 4, and 8. The device may include a housing formed of a lightweight, biologically inert material which need not be hermetically sealed. This is because, unlike most prior art infusion devices, the pressure source in the present device, which can be a propellant fluid, a mechanical spring or the like, or a combination of such elements, is contained in a separate enclosed container within the housing of the device, and the infusate, or drug to be administered, is stored outside the container containing the pressure source.

The container for the pressure source may be in the form of a variable volume container, such as a meal bellows, a flexible bag or envelope, or any other suitable variable volume container apparent to one of ordinary skill in the art. However, unlike an expandable balloon bag, the variable volume container may have a defined maximum and minimum volume. The infusate is administered to the patient from the device upon expansion of the variable volume container within the interior region of the housing until the variable volume container effectively fills the interior volume of the housing, at which point the infusate is substantially depleted.

The device can also be transcutaneously recharged with infusate without requiring that the device be removed from the patient. Recharging the infusate effectively recharges the pressure source by compressing the variable volume container to a reduced volume and creating pressure which is used to expel the infusate from the device.

The device may also include a separate bolus injection port for introduction of a bolus dose to the patient which bypasses the pressure source-driven delivery of the infusate from the principal reservoir of the device. Pierceable, self-sealing septa, through which infusate can be injected into the device, may be located in the primary and bolus ports of the device for convenient introduction and containment of infusate and bolus injections.

In addition, because the housing can be made of a lightweight material, such as plastic, many features, such as fluid flow channels, compartments, needle stops and suture loops, can be integrated into the housing during its manufacturer which can be accomplished by molding or other low-cost, high-volume manufacturing processes.

Figure 1:
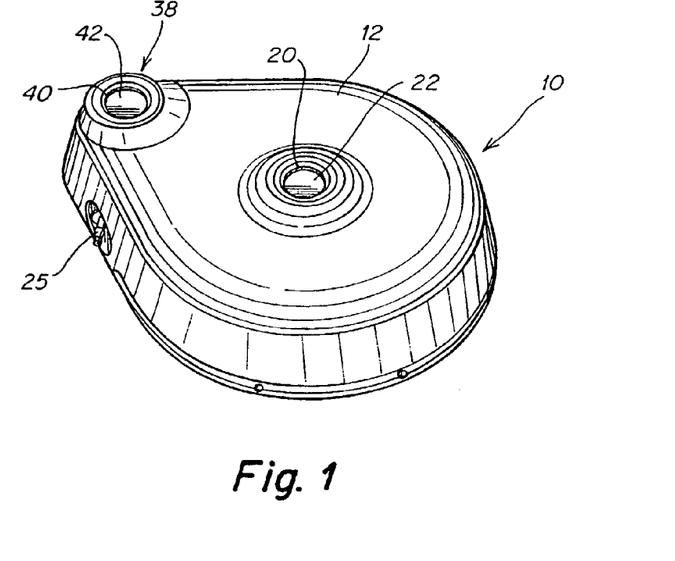
FIG. 1 is a perspective view of an infusion device according to one illustrative embodiment of the invention.
Figure 2:
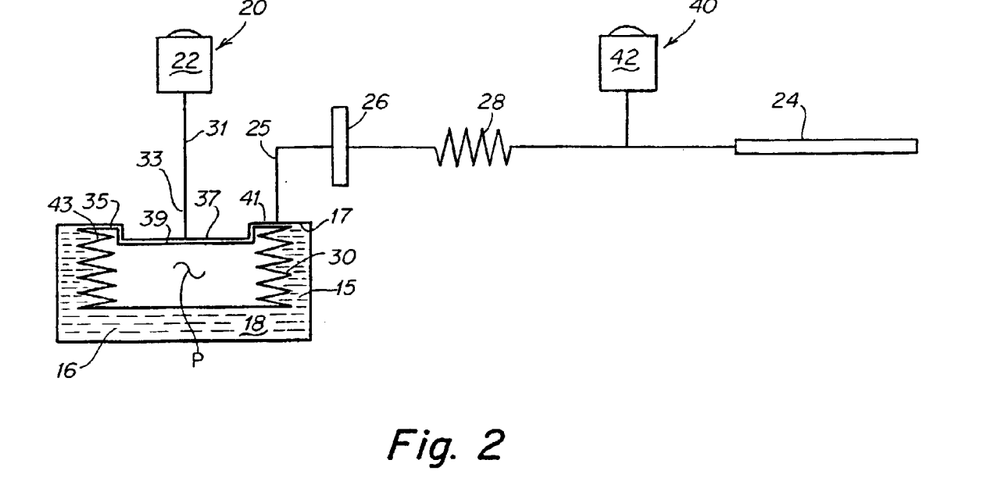
FIG. 2 is a schematic diagram of the device which illustrates its structure and principles of operation.
Figure 3:
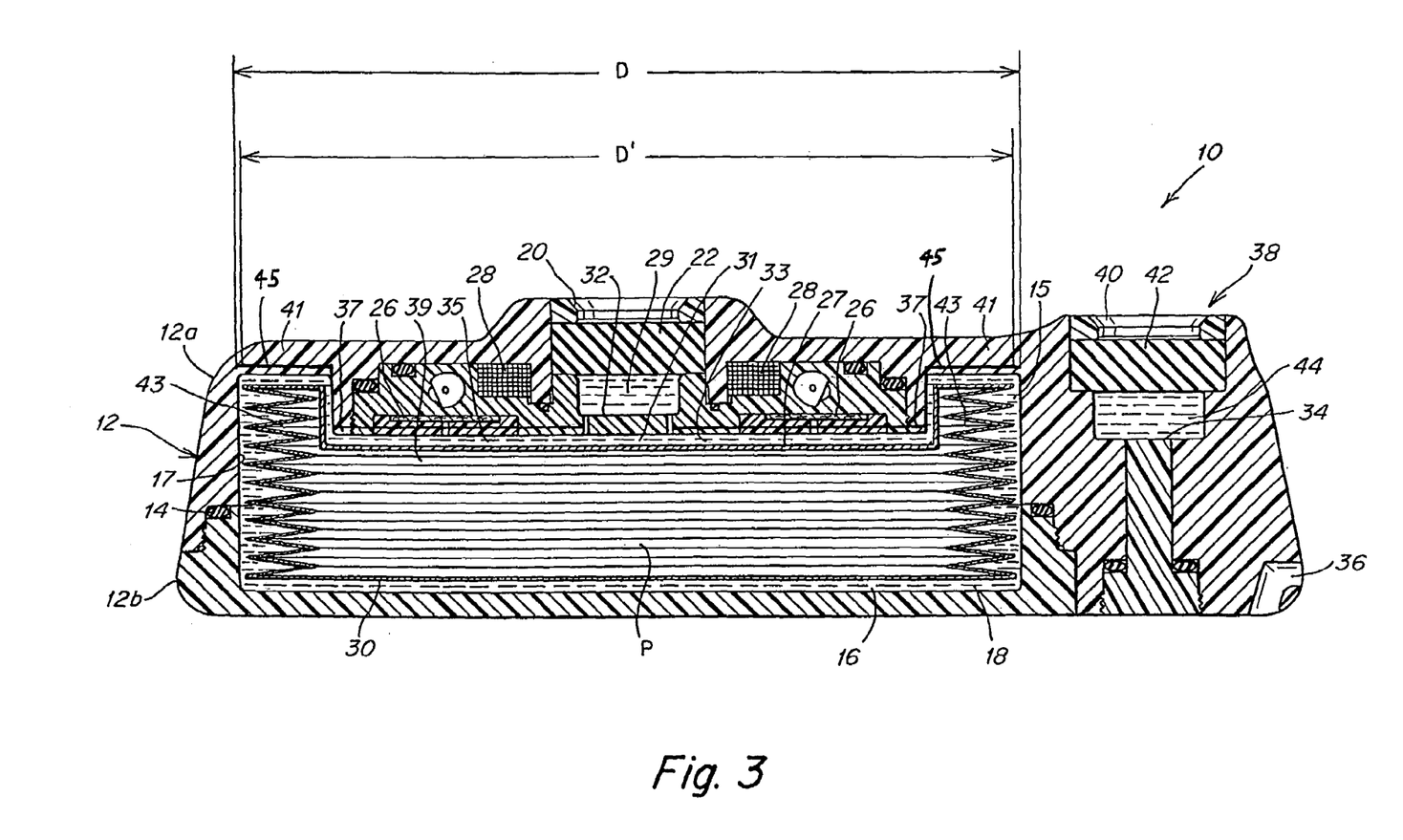
FIG. 3 is a sagittal view of the device of FIG. 1.
Figure 4:
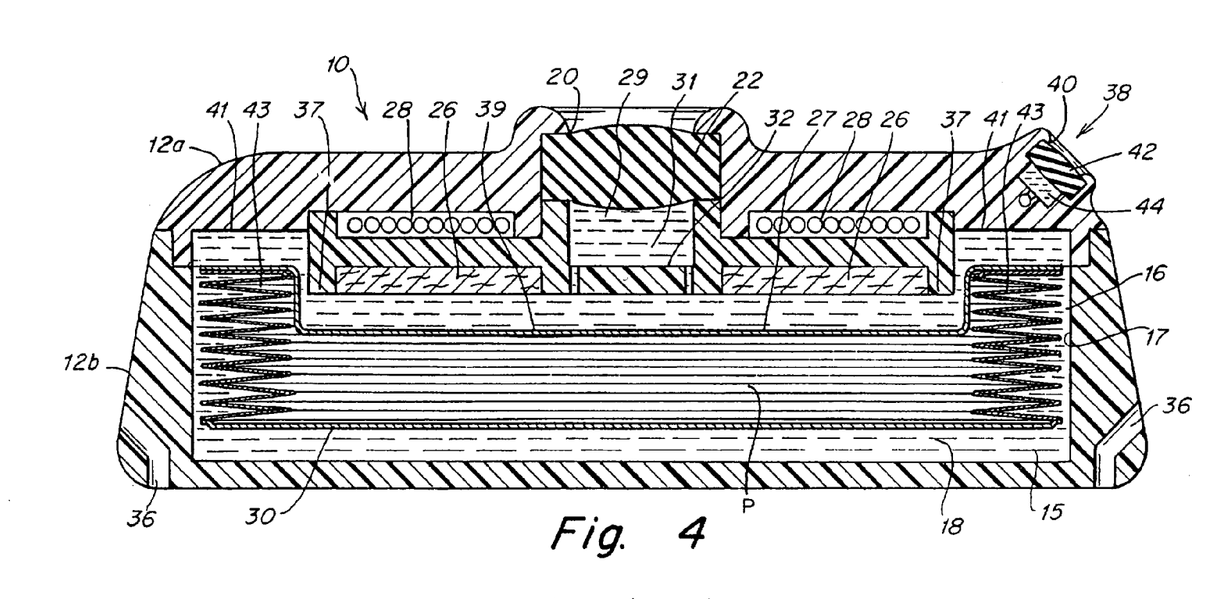
FIG. 4 is a sagittal view of an alternate design of the device, in which the sideport bolus port is located at an angle on a peripheral edge of the device.
Figure 5:
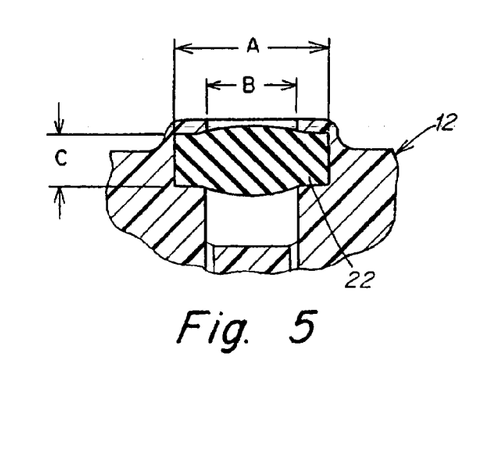
FIG. 5 is a sagittal view of a replaceable septum in a device according to one illustrative embodiment of the present invention.
Figure 6A:
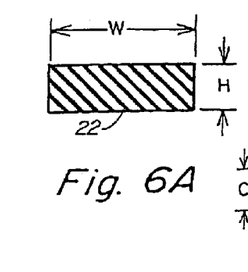
FIGS. 6A–6C illustrate one embodiment of a septum replacement kit and the steps for installing a replacement septum with a septum replacement tool.
Figure 6B:
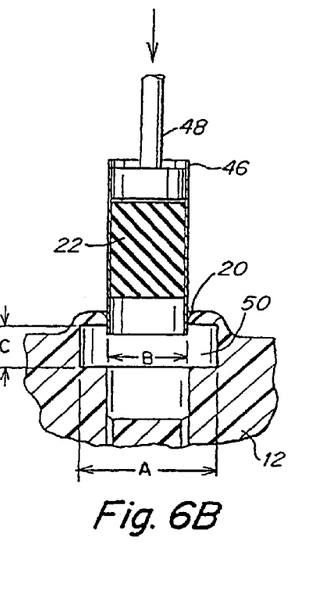
Figure 6C:
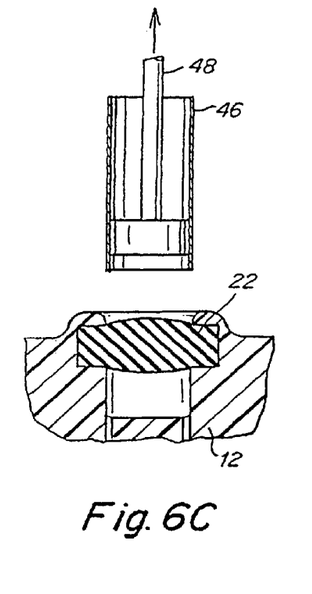
Figures 7A, 7B:
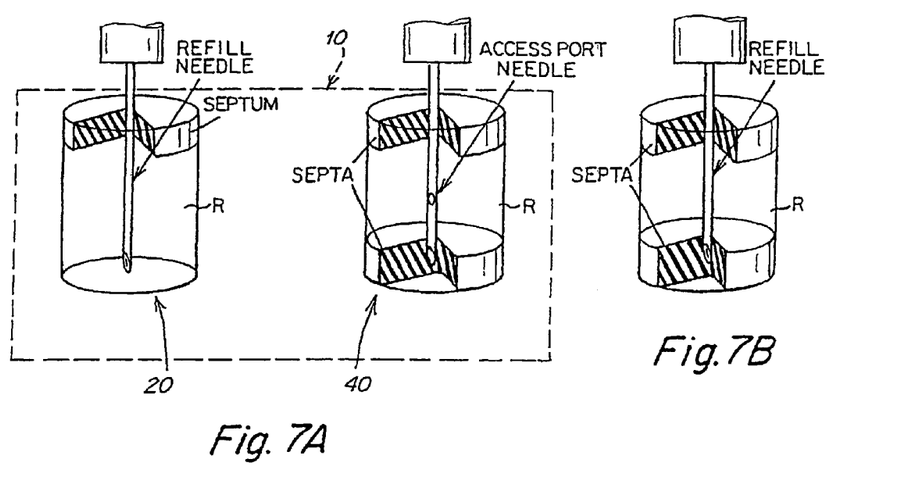
FIGS. 7A–7B illustrate one embodiment of a bolus port safety feature which prevents inadvertent administration of an overdose of drug to the patient through the bolus injection port.
Figure 8:
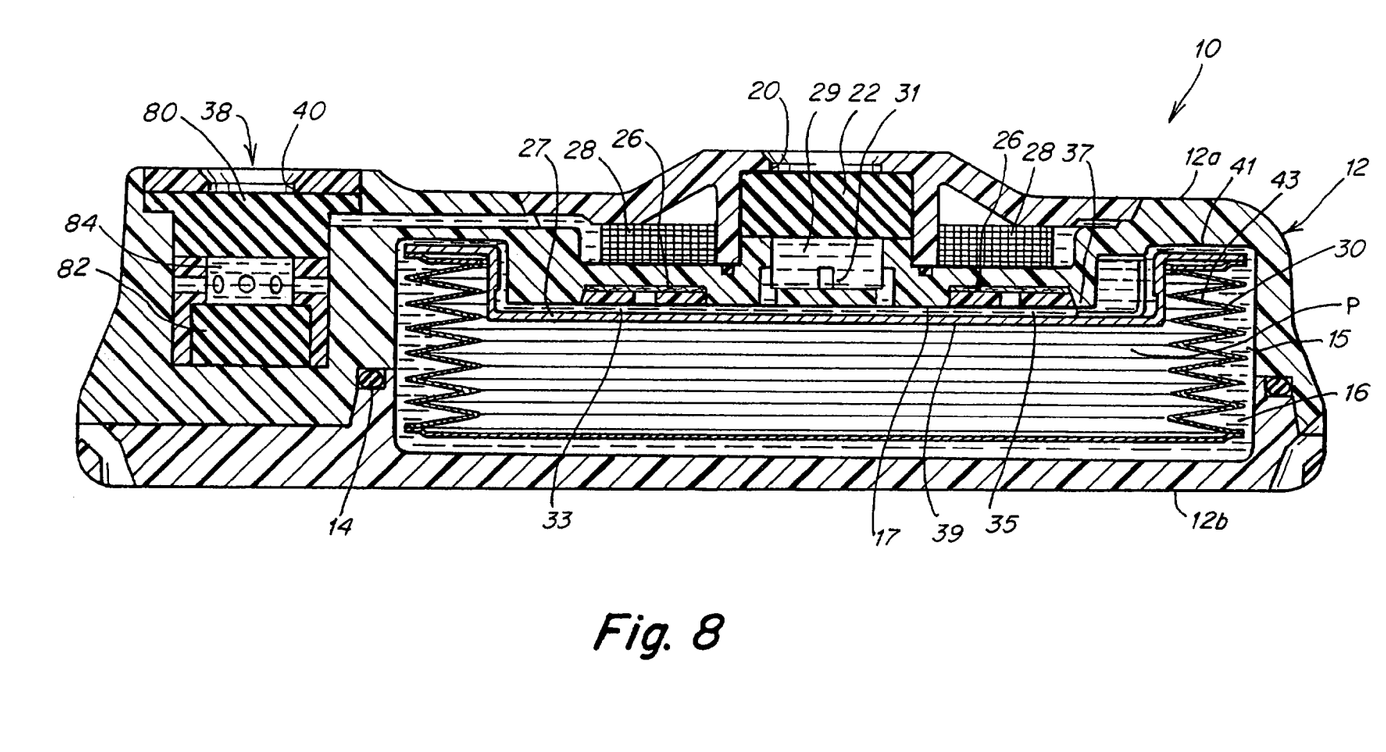
FIG. 8 is a sagittal view of another illustrative embodiment of the device.

FIG. 1 shows a perspective view of an infusion device 10 according to one illustrative embodiment of the invention. FIG. 2 illustrates in schematic form the basic structure and principle of operation of the device. FIG. 3 is a detailed sectional view of the device of FIG. 1 along a sagittal (vertical longitudinal) axis. FIG. 4 is a sagittal view of an alternate design of the device, in which the side bolus port is located at an angle from a top edge of the device. FIG. 5 is a sagittal view of a replaceable septum for the device. FIGS. 6A–6C illustrate one embodiment of a septum replacement kit and a method of using it to remove a worn septum and replace it with a fresh septum. FIGS. 7A–7B illustrate one embodiment of a bolus safety feature which prevents the inadvertent administration of a principal dose of the drug to be infused through the bolus injection port. FIG. 8 is a sagittal view of another illustrative embodiment of the device according to the present invention.

The device 10 includes a housing 12 which may be made of a lightweight, durable, and biologically inert material, such as plastic. The housing may be formed of an upper housing 12a and a lower housing 12b, which are joined with an o-ring 14 between them to create a fluid-impermeable seal. The halves of the housing can be joined by, for example, ultrasonic or thermal welding, solvent bonding, or other adhesive-based bonding.

The housing of the device defines an interior region 15 which forms a principal reservoir 16 for the infusate 18, which is typically a drug to be administered over a period of time at a constant flow dose to a patient into which the device has been surgically implanted. The infusate is introduced into the principal reservoir via a principal entry port 20, which is sealed with a pierceable, self-sealing septum 22. The infusate is delivered from the principal reservoir to a catheter 24 via an exit flow path 25.

A filter 26 may be provided along the exit flow path to remove particulates from the infusate as it is being delivered from the principal reservoir. It is to be appreciated that the device may employ any suitable filter apparent to one of skill in the art.

A flow restrictor 28 may be provided along the exit flow path to regulate flow of the infusate from the reservoir to the patient for a predetermined time period. The device may use any suitable flow restrictor apparent to one of skill in the art. For example, the flow restrictor may include a glass capillary flow restrictor, an etched silicone chip restrictor and the like.

It is to be appreciated that the flow restrictor may also include a programmable flow controlling device as would be apparent to one of skill in the art. Thus, the device can be preprogrammed or reprogrammed to deliver certain dosages to the patient.

In one preferred embodiment of the invention, the device can include a separate restrictor chamber in the upper housing 12a. This separate restrictor chamber permits the use of interchangeable restrictors for establishing different infusate flow rates.

Delivery of the infusate from the principal reservoir is driven by a pressure source P contained within an enclosed variable volume chamber 30. The chamber may be attached to an inner wall 17 of the housing, preferably to the upper housing 12a, as detailed more fully below. The chamber may also be coupled to the inner wall of the housing, such as by resting, or free floating within the housing. The pressure source may be a multiple-phase fluid which expands from a liquid phase to a gas phase with increasing temperature, thereby increasing in volume and pushing against the walls of the variable volume container to enlarge it, thereby decreasing the volume of the principal reservoir 16 and expelling the infusate therein from the device. Alternatively, the pressure source may be a mechanical device, such as a spring or other compressible member, or a shape-memory metal alloy. A combination of a propellant fluid and a compressible mechanical member may also be used to obtain a desired infusate delivery rate from the device. The mechanical member may, but need not, exert a constant force throughout its stroke range.

If a propellant fluid is used as the pressure source within the variable volume chamber, the chamber may be configured with a minimum volume that is greater than the liquid volume of the propellant fluid, so that the propellant fluid in the chamber remains in both liquid and gas phases when the chamber is compressed to its minimum volume. In addition, it may be desirable to select a propellant fluid which is at a pressure of not less than one atmosphere at ambient temperature, so that at the temperature of use (typically nominal body temperature of the patient) the propellant is at a pressure which is even higher than one atmosphere of pressure. This allows the surgeon to prime and operate the device at ambient temperature in order to verify its performance prior to implantation of the device in the patient, thereby eliminating the need to warm the device and the infusate to body temperature. In addition, such a positive pressure device substantially reduces the risk that outside air or gases will be drawn into the device during storage of the device. In one embodiment, the propellant fluid may include a refrigerant, such as a FREON-type fluid.

The inert plastic housing containing the infusate 18 may, but need not, be hermetically sealed. The housing, if made of a moldable or easily formed material, may include, for example, integrally formed needle stops 32, 34 for the primary and bolus injection sites, as well as one or more integrally formed suture loops 36 for passage of anchoring sutures therethrough when locating the device in a patient's body. An adhesion resistant material, such as silicone rubber or other suitable material, may be provided within the loops 36 to prevent tissue ingrowth thereto.

The variable volume chamber 30 may be a substantially rigid, gas-impermeable bellows structure, or other similar rigid-walled or spring-driven structure which occupies a volume which approximates the volume of the principal reservoir 16 when expanded. In one illustrative embodiment shown in FIGS. 3 and 4, the variable volume chamber 30 includes an accordion-type bellows. It is to be appreciated that any suitable chamber may be employed for enclosing the pressure source of the device. Preferred materials for the bellows chamber may include, but are not limited to, metals and plastics.

Operation of the infusion device may be affected by the width dimension or diameter D' of the variable volume chamber relative to the diameter D of the housing. It may be desirable to have D' be less than D, so that the bellows walls are spaced from the housing walls, but preferably only by so much as will allow the bellows walls to move freely within the housing. The bellows walls may be located as close as possible to the housing walls so that substantial displacement of infusate can be achieved by movement of the bellows in the reservoir. However, it is desirable to avoid drag of the bellows walls on the housing walls. Thus, the variable volume chamber may be centered in the principal reservoir for increased volume and avoidance of drag and so that the distance D–D' is sufficient to avoid such drag.

Although the device and bellows are illustrated as cylindrical in a preferred embodiment, they may have any convenient shape.

The variable volume chamber may be located so that it does not obstruct the principal entry port 20 for infusate when the principal reservoir is empty and the variable volume chamber is at its expanded volume. In one embodiment, the variable volume chamber 30 may be attached to the housing so as to define a recharging fluid flow path 31 between the variable volume chamber and the housing that is adapted to carry infusate from outside the housing through the principal entry port 20 to the interior region 15 of the housing. A fluid recharging reservoir 29 may be provided along the recharging fluid flow path 31 to hold the infusate before it flows into the interior region of the housing. A fluid dispersal flow path 33 may be provided along the recharging fluid flow path 31 at a coupling region 35 between the housing and the bellows to disperse the infusate into the interior region of the housing. Alternatively, the chamber 30 and housing 12 may be designed to share a common wall which may be channeled to provide fluid flow paths along the interface between the housing and the chamber 30. In still another alternate embodiment, the bellows may be freely located in the interior region of the housing.

A spacer 27 may be provided on either the housing, the bellows or both, such that the recharging fluid flow path is not obstructed by movement of the bellows. The spacer may be any device or method apparent to one of skill in the art to maintain the recharging fluid flow path unobstructed by the bellows, such as channels, grooves or standoffs. For example, in one embodiment, the free bellows may be held away from the infusate entry port by standoffs extending from the bellows or from the infusate entry port.

To ensure as low a profile as possible for the device, it may be desirable to construct the housing so that the central portion 37 of one or both of its top and bottom portions, along with corresponding central portions or regions 39 of the top and bottom members of the bellows, is offset or depressed from the nominal plane of the central portions as shown in FIGS. 3 and 4 to form a nested structure. The infusate entry port nests within a recessed central portion of the bellows.

As illustrated, the central portions or regions 37 and 39 of the top and bottom portions of the housing and/or the bellows may be surrounded by annular peripheral portions or regions 41, 43. Although only the top portions of the housing and bellows are shown as nested in FIGS. 3 and 4, the bottom portions of the housing and bellows could also be nested to further reduce the height of the device. Reductions in the volume of the infusate chamber 30 reduce the amount of infusate that can be administered and increase the frequency with which the chamber 30 may need to be recharged if drug delivery is to take place over an extended period. However, the pressure source can be selected so as to maximize delivery from a given volume.

As illustrated in FIGS. 1–4, the device may include a separate bolus injection port 38, which includes a bolus entry port 40 sealed with a pierceable, self-sealing septum 42. The bolus entry port 40 leads to a bolus reservoir 44, which is in fluid communication with the fluid exit flow path 25 and delivery catheter 24, yet downstream of the filter 26 and flow restrictor 28. Infusate introduced into the bolus port goes directly into the delivery catheter and bypasses the controlled release provided by the action of the pressure source and variable volume chamber on the infusate in the principal reservoir.

Both the principal infusate entry port 20 and the bolus injection port 38 may include sensing devices known in the art which assist the patient and medical staff in locating the devices transdermally so that additional infusate can be introduced to the device without the need for external palpation or surgical removal of the device.

The life of an implantable infusion device, such as those described herein, is determined in large part by the life of the septum through which the infusate is introduced. Use of a self-sealing material, such as an elastomer, silicone rubber or similar material, for the septum allows the septum to reseal after it has been pierced with a needle. However, even self-sealing materials lose some elasticity after a certain number of uses and may require replacement to ensure that no infusate leaks out of the device.

Septum life, and thus infusion device life, can be optimized by careful selection of the septum material and the dimensions of the septum and the septum chamber in the device. This is shown in FIG. 5. The ratio of the opening dimension of the septum chamber (B) to the width of the septum chamber (A) preferably is such that the entire septum volume can fit within the chamber opening B when the septum is compressed, and such that the chamber width A adequately compresses the septum to provide satisfactory puncture life. The selection of a material for the septum may also be a consideration, as its hardness, as measured by a durometer preferably allows for adequate compression of the septum during insertion without comprising puncture life. The height of the septum chamber (C) preferably is sufficient to permit the compressed septum to fill the chamber and still be sufficiently axially compressed to achieve the desired puncture life.

A septum replacement kit allows the surgeon to replace a worn septum without surgically removing the device from the patient. Such a kit is illustrated in FIGS. 6A–6C. FIG. 6A shows a septum 22, which is typically in the form of a cylindrical or square plug of height H and width W. The septum may be made of a compressible, resilient, penetrable, self-sealing material, such as a rubber or elastomer. FIG. 6B shows the septum lodged in a tubular member 46, which is sized to fit into the entry port 20, having width B, of the infusion device 12. The septum is easily compressed sufficiently to be lodged into the tubular member 46, and a plunger 48 is used to dislodge the septum from the tubular member into the septum chamber 50, which has width A and height C, after it is inserted into the entry port 20, as shown in FIG. 6C. The septum is radially compressed in the chamber to form a penetrable seal. The plunger and tubular member can then be withdrawn.

Removal of a worn septum can be accomplished by inserting a sharp instrument into the septum to cut it into sections that can then be removed Mom the septum chamber with tweezers or other suitable instrument.

Although FIGS. 6A–6C illustrate use of the septum replacement kit for replacing the primary septum 22, it should be understood that the kit can also be used to replace the bolus septum 42 in the bolus entry port 40.

The device may include a safety filling device to ensure that the patient and medical staff can distinguish between the primary entry port and the bolus injection port so as to reduce the incidence of an inadvertent administration of relatively large doses intended to be administered over time to the patient. When an implanted infusion pump is to be refilled, it may be difficult to determine whether a refill needle is positioned to enter the principal infusate port 20 or the bolus injection port 38. Entry of the refill needle into the wrong port for the dose being administered can result in a patient receiving an excessive dose of the drug and therefore is desirably prevented.

A bolus safety feature in accordance with one illustrative embodiment of the present invention is shown and described in connection with FIGS. 7A–7B. FIG. 7A illustrates the two infusate ports in a typical implantable infusion pump according to the invention. The device includes a principal, or center, access port 20 for administration of infusate into the device, and a bolus access port 40 for administration of a bolus injection directly to the patient. The center access port 20 includes a single septum, below which is disposed an infusate reservoir R. To fill the center access port 20, a refill needle having a hole in the tip, as shown, is used.

In contrast, the side bolus access port 40 includes two septa which are spaced apart to define an infusate reservoir R between them. The top septum in the bolus access port 40 secures the delivery needle in place and provides a seal to prevent leakage of the bolus dose once the needle is removed from the bolus port. The bottom septum blocks the opening in the tip of a standard refill needle, as shown at 20, should such a needle be inadvertently inserted into the bolus port. A special needle with a side-access opening displaced from the tip or near the center of its length, as shown at 40, instead of at or near the tip, as shown at 20, can be used to fill the bolus port.

FIG. 7B shows the result of using a standard delivery needle in the bolus port. The standard delivery needle includes an opening at its tip and no opening in the side. The opening in the tip will be blocked by the lower septum when the needle is inserted into the bolus port, and no infusate will be delivered.

This design of the center and bolus ports in the device of the invention assists in avoiding a bolus dose from being administered inadvertently to a patient, because a bolus (side-access opening) needle is used in the bolus port. If a standard delivery needle is accidentally inserted into the bolus port, no infusate can be delivered, and the surgeon can recognize that the wrong needle is being used, without administering any harmful dose to the patient.

FIG. 8 illustrates an infusion device 10 according to another illustrative embodiment of the present invention. The device 10 includes a housing 12 formed of an upper housing 12a and lower housing 12b similar to that described above with reference to the illustrative embodiments of FIGS. 3 and 4.

The housing 12 of FIG. 8 defines an interior region 15 which forms a principal reservoir 16 for the infusate. The infusate is delivered into the reservoir 16 through a fluid recharging flow path. The housing also includes an exit fluid flow path 25 to direct the infusate from the principal reservoir to a delivery catheter 24 as described above (see FIG. 1). An enclosed variable volume chamber 30 is contained within an interior region 15 of the housing for exerting pressure within the reservoir to expel infusate therefrom. As shown, the variable volume chamber is attached to the top of the housing.

A coupling region 35 may be formed between a portion of an inner wall 17 of the housing and the variable volume chamber. Additionally, a fluid dispersal flow path 33 may be provided in the recharging fluid flow path 31 at the coupling region to disperse the fluid into the principal reservoir.

As shown in FIG. 8 and described above, the offset central portion of the housing 37 substantially nests within the offset central region 39 of the variable volume chamber to reduce the profile of the housing. The fluid dispersal flow path may be provided between the central portion of the housing 12 and the central region of the variable volume chamber 30.

The illustrative embodiment of the device 10 shown in FIG. 8 includes a separate bolus injection port 38 in fluid communication with the exit fluid flow path, such that it bypasses the principal reservoir. The bolus port is sealed with a pair of self-sealing septa 80, 82, as described above with reference to FIGS. 7A–7C, that are spaced apart within the bolus port to form a bolus reservoir 84. Because the septa are spaced apart, a delivery needle having an opening displaced from a tip of the needle is used to deliver a bolus of drug to the bolus reservoir. It is to be appreciated, however, that any suitable safety feature apparent to one of skill in the art may be employed to reduce the incidence of inadvertently delivering a harmful dose of infusate to the bolus reservoir.

Because certain changes may be made in the above apparatus without departing from the scope of the invention herein disclosed, it is intended that all matter contained in the above description or shown in the accompanying drawings shall be interpreted in an illustrative and not a limiting sense.

What is claimed is:

1. An implantable infusion device, comprising:
a housing including an inner wall and having an interior region defined at least in pat by the inner wall, at least a portion of the interior region defining an infusate reservoir adapted to store an infusate therein for delivery to a patient;

a closed free-floating variable volume chamber having an outer wall, the variable volume chamber disposed within the interior region of the housing with the outer wall of the variable volume chamber being spaced from the inner wall of the housing, the variable volume chamber being supported within the interior region from an internal portion of the inner wall of the housing;

a pressure source contained within the variable volume chamber;

an infusate recharging fluid flow path adapted to recharge the infusate reservoir by carrying infusate to the infusate reservoir through the internal portion of the housing from which the variable volume chamber is supported within the interior region; and an exit fluid flow path adapted to deliver infusate from the infusate reservoir out of the housing.

2. The implantable infusion device according to claim 1, wherein the infusate reservoir substantially surrounds the chamber.

3. The implantable infusion device according to claim 1, wherein the housing includes a top portion and a bottom portion connected by an annular portion, the variable volume chamber being supported within he interior region from one of the top and bottom portions of the housing.

4. The implantable infusion device according to claim 3, wherein the exit fluid flow path is provided adjacent to the annular portion of the housing and adapted to deliver infusate from the infusate reservoir out of the housing.

5. The implantable infusion device according to claim 1, further comprising a pierceable, self-sealing septum disposed in the infusate recharging fluid flow path.

6. The implantable infusion device according to claim 5, further comprising an infusate recharging fluid reservoir disposed along the infusate recharging fluid flow path.

7. The implantable infusion device according to claim 1, wherein the housing is made of gas-impermeable material.

8. The implantable infusion device according to claim 1, wherein the pressure source includes one or more of the group consisting of a multiple-phase fluid, a spring, a shape memory device, a Belville washer, and a compressible material.

9. The implantable infusion device according to claim 1, wherein the exit fluid flow path is adapted to deliver the infusate from the infusate reservoir out of the housing.

10. The implantable infusion device according to claim 9, further comprising a flow restrictor disposed along the exit fluid flow path.

11. The implantable infusion device according to claim 9, further comprising a filter disposed along the exit fluid flow path.

12. The implantable infusion device according to claim 9, wherein the pressure source includes a multiple-phase fluid propellant that exists in at least one of a liquid phase and a gas phase within the variable volume chamber as a function of ambient temperature, wherein conversion of the propellant from a liquid phase to a gas phase increases the volume displaced by the variable volume chamber in the interior region of the housing, thereby exerting a force on the infusate in the infusate reservoir so as to provide a substantially constant flow rate of the infusate out of the housing through the exit fluid flow path.

13. The implantable infusion device according to claim 12, wherein the propellant is disposed in the variable volume chamber at a pressure which is not less than atmospheric pressure at ambient temperature.

14. The implantable infusion device according to claim 9, further comprising a bolus port in fluid communication with the exit fluid flow path.

15. The implantable infusion device according to claim 14, further comprising a pair of septa disposed in the bolus port wherein the septa are spaced apart to define a bolus reservoir therebetween that is adapted to receive a bolus dose deliverable thereto using a delivery needle having an opening displaced from a tip of the needle.

16. The implantable infusion device according to claim 1, wherein the variable volume chamber is made of a substantially rigid, gas-impermeable material.

17. The implantable infusion device according to claim 1, wherein the variable volume chamber is hermetically sealed.

18. The implantable infusion device according to claim 1, further comprising a support region between the internal portion of the housing and the variable volume chamber, the support region including a fluid dispersal flow path to direct infusate along the infusate recharging fluid flow path to the infusate reservoir.

19. The implantable infusion device according to claim 1, wherein the variable volume chamber includes an annular peripheral region disposed about a central region thereof, the central region being offset from a plane defined by the annular peripheral region of the variable volume chamber.

20. The implantable infusion device according to claim 19, further comprising a support region between the internal portion of the housing and the variable volume chamber, the support region including a fluid dispersal flow path adjacent the central region of the variable volume chamber to direct fluid along the infusate recharging flow path to the infusate reservoir.

21. The implantable infusion device according to claim 20, wherein the fluid dispersal flow path includes regions of increased surface contact area in the support region between the housing and the variable volume chamber.

22. The implantable infusion device according to claim 19, wherein the recharging fluid flow path includes at least one channel between the variable volume chamber and the housing extending adjacent from the central region to the annular peripheral region of the variable volume chamber.

23. The implantable infusion device according to claim 19, wherein the internal portion of the housing includes a central portion and an annular peripheral portion disposed about the central portion, the central portion being offset from a plane defined by the annular peripheral portion of the housing, wherein the central portion of the housing substantially nests within the central region of the variable volume chamber.

24. The implantable infusion device according to claim 23, wherein the housing includes a fluid dispersal flow path between the central portion of the housing and the central region of the variable volume chamber.

25. The implantable infusion device according to claim 1, wherein the variable volume chamber includes an accordion-type bellows.

26. The implantable infusion device according to claim 25, wherein the bellows includes a plurality of serially coupled annular members extending between top and bottom portions thereof.

27. The implantable infusion device according to claim 26, wherein junctions of the coupled annular members are coupled with flexures.

28. The implantable infusion device according to claim 1, wherein the interior region and the variable volume chamber are substantially cylindrical.

29. The implantable infusion device according to claim 1, wherein the housing includes at least one integral suture loop.

30. An implantable infusion device, comprising:
a housing including an inner wall and having an interior region defined at least in part by the inner wall, at least a portion of the interior region defining an infusate reservoir adapted to store an infusate therein for delivery to a patient;
a closed free-floating variable volume chamber having an outer wall, the variable volume chamber disposed within the interior region of the housing with the outer wall of the variable volume chamber being spaced from the inner wall of the housing, the variable volume chamber being supported within the interior region from an internal portion of the inner wall of the housing;
a pressure source contained within tie variable volume chamber;
an infusate recharging fluid flow path adapted to recharge the infusate reservoir by directing infusate into the infusate reservoir; an exit fluid flow path adapted to carry infusate from the infusate reservoir out of the housing; and
a bolus port in fluid communication with the exit fluid flow path.

31. The implantable infusion device according to claim 30, wherein the bolus port includes a pair of septa spaced apart to define a bolus reservoir therebetween that is adapted to receive a dose of bolus deliverable thereto using a delivery needle having an opening displaced from a tip of the needle.

32. The implantable infusion device according to claim 30, further comprising a pierceable, self-sealing septum disposed in the infusate recharging fluid flow path.

33. The implantable infusion device according to clam 32, further comprising a recharging fluid reservoir disposed along the infusate recharging fluid flow path.

34. The implantable infusion device according to claim 30, wherein the housing is made of gas-impermeable material.

35. The implantable infusion device according to claim 30, wherein the pressure source comprises one or more of the group consisting of a multiplephase fluid, a spring, a shape memory device, a Belville washer, and a compressible material.

36. The Implantable infusion device according to claim 30, further comprising a flow restrictor disposed along the exit fluid flow path.

37. The implantable infusion device according to claim 30, further comprising a filter disposed along the exit fluid flow path.

38. The implantable infusion device according to claim 30, wherein the pressure source includes a multiple-phase fluid propellant that exists in at least one of a liquid phase and a gas phase within the variable volume chamber as a function of ambient temperature, wherein conversion of the propellant from a liquid phase to a gas phase increases the volume displaced by the variable volume chamber in the interior region of the housing, thereby exerting a force on the infusate in the infusate reservoir so as to provide a substantially constant flow-rate of the infusate out of the housing through the exit fluid flow path.

39. The implantable infusion device according to claim 38, wherein the propellant is disposed in the variable volume chamber at a pressure which is not less than atmospheric pressure at ambient temperature.

40. The implantable infusion device according to claim 30, wherein the variable volume chamber is made of a substantially rigid, gas-impermeable material.

41. The implantable infusion device according to claim 30, wherein the variable volume chamber is hermetically sealed.

42. The implantable infusion device according to claim 30, wherein the variable volume chamber includes an accordion-type bellows.

43. The implantable infusion device according to claim 30, wherein the interior region and the variable volume chamber are substantially cylindrical.

44. The implantable infusion device according to claim 30, wherein the housing includes at least one integral suture loop.

45. An implantable infusion device, comprising:
a housing including an inner wall and having an interior region defined at least in part by the inner wall, at least a portion of the interior region defining an infusate reservoir adapted to store an infusate therein for delivery to a patient;
a closed variable volume chamber free-floating within the interior region of the housing;
a pressure source contained within the variable volume chamber;
a fluid flow path adapted to carry infusate between a point external to the housing and the interior region of the housing; and
a spacer supported by at least one of the housing and the variable volume chamber to maintain the fluid flow path unobstructed by the variable volume chamber.

46. The implantable infusion device according to claim 45, wherein the spacer includes a groove provided on the at least one of the housing and the variable volume chamber.

47. The implantable infusion device according to claim 45, wherein the spacer includes at least one standoff.

48. The implantable infusion device according to claim 45, wherein the spacer is at least in part molded on the at least one of the housing and the variable volume chamber.

49. The implantable infusion device according to claim 45, wherein the fluid flow path is an infusate recharging fluid flow path.

* * * * *